United States Patent [19]

Kanda et al.

[11] Patent Number: 5,246,006
[45] Date of Patent: Sep. 21, 1993

[54] APPARATUS FOR ULTRASONIC COLOR FLOW MAPPING

[75] Inventors: Hiroshi Kanda, Tokorozawa; Shinichiro Umemura, Hachioji; Hisashi Nishiyama, Tokyo; Ryuichi Shinomura, Higashimatsuyama; Kageyoshi Katakura, Tokyo; Shizuo Ishikawa, Kanagawa; Koji Tanabe; Satoshi Tamano, both of Kashiwa, all of Japan

[73] Assignee: Hitachi Medical Corporation, Tokyo, Japan

[21] Appl. No.: 781,840

[22] Filed: Oct. 24, 1991

[30] Foreign Application Priority Data

Oct. 24, 1990 [JP] Japan .................. 2-284288
Feb. 20, 1991 [JP] Japan .................. 3-047487
Feb. 21, 1991 [JP] Japan .................. 3-049156

[51] Int. Cl.⁵ .................................... A61B 8/06
[52] U.S. Cl. .................. 128/661.09; 128/660.05
[58] Field of Search .......... 128/660.05, 661.08–661.10; 73/861.25

[56] References Cited

U.S. PATENT DOCUMENTS 4,761,740 8/1988 Lipschutz .
4,911,171 3/1990 Uchibori ................... 128/661.09
4,932,415 6/1990 Angelsen et al. .......... 128/661.09
5,031,628 7/1991 Nakamura et al. ........ 128/661.09
5,042,491 8/1991 Amemiya ................. 128/661.09
5,078,146 1/1992 Sato ....................... 128/661.09 X

FOREIGN PATENT DOCUMENTS 346890 6/1989 European Pat. Off. .
3827513 8/1989 Fed. Rep. of Germany .
2-119849 10/1983 Japan .
60-96232 5/1985 Japan .

Primary Examiner—Francis Jaworski
Attorney, Agent, or Firm—Antonelli Terry Stout & Kraus

[57] ABSTRACT

An ultrasonic flow mapping apparatus transmits and reflects waves from sampling points on a two-dimensional cross-section. The waves are detected while transmitting repeatedly ultrasonic pulses. The phase shifts of different reflected waves are calculated, and displayed in color to show a distribution of blood flow velocity. Artifact due to reflected waves from body organs, which remain even by using MTI filters, is detected from phase signals, which have not passed through the MTI filters, and the artifact is removed by lowering display brightness for a sampling point corresponding to a relevant detection output.

11 Claims, 4 Drawing Sheets

APPARATUS FOR ULTRASONIC COLOR FLOW MAPPING

BACKGROUND OF THE INVENTION

The present invention relates to an apparatus for ultrasonic color flow mapping for diagnosis use, and in particular to an apparatus and a method capable of removing artifact due to movement of body organs to obtain correct display of blood flow.

An ultrasonic flood flow mapping apparatus displays the velocity and the direction of blood flow in a heart or an abdominal region two-dimensionally, using the Doppler effect. Since it is possible to recognize visually distribution of blood vessel in a living body by superposing an image thus obtained on a section image to display them together, it is often utilized at present in clinical sites. For example, JP-A-60-96232 (1985) discloses this technique.

In this apparatus, reflected waves from sampling points on a B-mode section are detected one after another by transmitting and receiving repeatedly ultrasonic pulses accompanying beam scanning to obtain phase signals indicating the phase of detected signals by complex data processing one after another. The phase shift of a signal from a sampling point corresponding to a specified transmission interval is calculated to obtain the velocity of a moving target at that point. Variations in this velocity are represented by numerical values or a graph, which are displayed at respective positions corresponding to the B-mode section, superposed on a B-mode image. In order to avoid influences of signals from body organs such as vessel wall, etc. on values representing this displacement velocity, digital filters having high pass characteristics called delay line cancelers or MTI filters (moving target indicating filters) are used. The velocity thus displayed is supposed to represent the blood flow velocity in a blood vessel.

Apart therefrom various blood flow mapping apparatuses have been proposed. For example, devices have been made, by which the B-mode step loading is displayed in a gray scale and the blood flow velocity superposed thereon is displayed in different color tones, etc.

In the field of diagnosis of the abdominal region such as the liver, the kidney, etc., blood flow information of extremely low velocity, which is as low as about 3 cm/sec is useful. It is difficult to separate signals for blood flow of this degree of velocity from signals due to movement of body organs themselves produced by movement of body, respiration, etc. by means of MTI filters having high pass characteristics as used heretofore. That is, if the band of the signal cut in the neighborhood of a point, where the phase shift is zero, is extended, blood flow information of low velocity is removed also by the MTI filters. On the contrary, if the band of the signal cut is narrowed, signal components due to movement of the body organs are mixed in the flow velocity signal and therefore artifact is mixed in the blood velocity display.

SUMMARY OF THE INVENTION

Therefore an object of the present invention is to provide a flow mapping apparatus capable of separating more properly signals indicating movement of body organs from signals indicating the blood flow velocity to remove effectively artifact due to movement of the body organs.

Another object of the present invention is to provide a flow mapping apparatus capable of displaying correctly distribution of the blood flow velocity in a low velocity region.

One of the most remarkable features of the present invention consists in judging, whether artifact due to movement of body organs is mixed in velocity detection signals or not, by using ultrasonic phase signals, which have not passed through MTI filters.

More concretely speaking, a first feature of the present invention consists in a construction, in which it comprises a first velocity calculator for calculating a velocity from an ultrasonic phase signal, which has passed through an MTI filter; a second velocity calculating device for calculating a velocity from an ultrasonic phase signal, which has not passed through the MTI filter; and indication control means, which permits the display of outputs of the first velocity calculator for corresponding sampling points, when the output of the second velocity calculator exceeds a first threshold, and permits the display of the outputs of the first velocity calculator for the corresponding sampling points, only when the output of the second velocity calculator is below the first threshold.

The indication control means includes means for detecting the power of the ultrasonic phase signal, which has not passed through the MTI filter, and logic means for canceling the prohibition of display described above, when the power thus detected is below a second threshold.

The output of the first velocity calculating device obtained from the ultrasonic phase signal, which has passed through the MTI filter, indicates, in general, principally the blood flow velocity. Artifacts may be mixed therein, when reflected waves from the body organs are strong or when the velocity of movement of the body organs is at a certain high level, and that contrarily thereto, the output of the second velocity calculator obtained from the ultrasonic phase signal, which has not passed through the MTI filter, indicates always approximately only the velocity of movement of the body organs, i.e. only an artifact signal. According to the first feature described above, when the velocity of movement of the body organs is at a certain high level, since it is precisely detected that the artifact is mixed in the output of the first velocity calculator and the display is prohibited, it is possible to display blood flow velocity distribution, from which the artifact due to movement of the body organs themselves is effectively removed.

By an analysis more in detail, it was found that in the case where power of the ultrasonic phase signal, which has not passed through the MTI filter, is very low, reflected waves from blood flow is predominant rather than reflected waves from the body organs and even if the velocity indicated by the second velocity calculator is high, artifact is not mixed in the output of the first velocity calculator. Therefore, by the second feature described above it can be prevented to remove erroneously a velocity detection output, in which no artifact is mixed. According to these features, even if the band of low velocity region out of the MTI filter is narrowed, since the artifact due to movement of the body organs themselves can be removed effectively, a blood flow distribution is obtained precisely up to the low velocity region.

A third feature of the present invention consists in that the first threshold described previously is given as a function relating to the output of the power detecting means described above. That is, the smaller the power of the ultrasonic phase signal is, which has not passed through the MTI filter, the higher the threshold for the display prohibition is made with respect to the output. In this way it can be judged more properly whether the artifact is mixed in the output of the first velocity calculator or not and it is possible to remove precisely the artifact. For judging whether the artifact is mixed therein or not, apart from the method, by which the magnitude of the power of the ultrasonic phase signal, which has not passed through the MTI filter, is taken into account, as described above, another method is also possible, by which turbulence in the velocity, i.e. representatively variance of a plurality of velocity signals for a same sampling point, coming from the second velocity calculator, is taken into account. That is, since reflected waves from the blood flow are predominant, when the turbulence in the velocity or the variance $\sigma^2$ of the velocity signal, the prohibition of the display by the magnitude of the velocity given by the second velocity calculator is canceled and the first threshold for the display prohibition is increased.

Further, a construction is also useful, in which all of the velocity detection value, the power detection value and the turbulence detection value obtained from the ultrasonic phase signal, which has not passed through the MTI filter, which have been described previously, are used for the judgement of the presence or absence of the mixing of the artifact after having made the processed phase signal pass through a smoothing filter.

Other features of the present invention will be made clear by explanation of some preferred embodiments.

DESCRIPTION OF THE PREFERRED EMBODIMENTS

Figure 1:
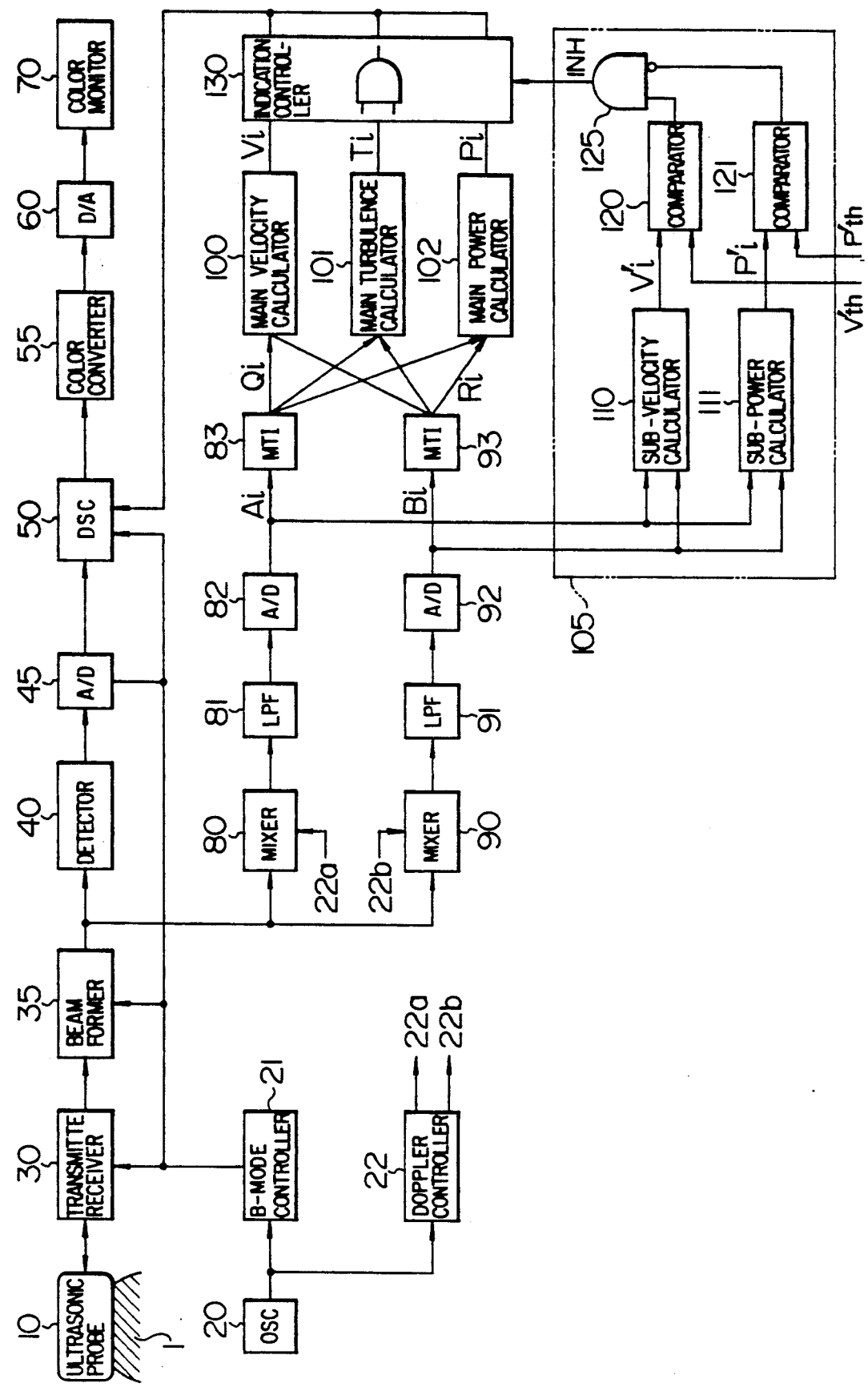
FIG. 1 is a block diagram showing an embodiment of the present invention.

FIG. 1 shows the whole construction of a ultrasonic blood flow mapping apparatus in a first embodiment of the present invention. An ultrasonic probe 10 applied to a surface of a living body 1, which is an object to be measured, includes an ultrasonic transducer array and these transducers are connected with a transmitter/receiver 30. The transmitter/receiver 30 is controlled by a B-mode display controller working on the basis of a master clock issued from a clock oscillator 20 and in this way the transmitter/receiver 30 drives the transducer array in the ultrasonic probe by the B-mode electronic scanning method. That is, ultrasonic pulses are issued repeatedly from the ultrasonic probe 10 so that a focused ultrasonic beam scans predetermined cross-sections traversing the living body 1 one after another. Reflected waves produced by different ultrasonic pulses are received by the transducer array in the ultrasonic probe 10 and a received signal is led to a beam former 35 through the transmitter/receiver 30. The beam former 35 is controlled also by the B-mode controller 21. In this way the output of the beam former 35 is also a received signal reflecting the ultrasonic beam scanning the observed section, similarly to the transmitted ultrasonic pulses. This received signal is detected by a detector 40 and converted into a digital signal by an A/D converter 45. The received signal thus digitized is written in a digital scan converter 50 having a two-dimensional memory corresponding to the whole observed section. When one cycle of scanning is terminated, data indicating one ultrasonic B-mode image are completed in the digital scan converter 50 and these data are up-dated successively by repeating the scanning.

On the other hand, data of blood flow distribution displayed, superposed on this B-mode image are obtained by a Doppler analyzer after blocks 80 and 90. At first, the received signal from the beam former is mixed with reference signals 22a and 22b having a phase difference of 90° generated by a Doppler controller 22 in mixers 80 and 90, respectively. Low frequency components of mixed signals thus obtained are extracted by low pass filters 81 and 91, respectively. They are sampled by A/D converters 82 and 92 and thus complex data $A_i$ and $B_i$ indicating the amplitudes and the phases of the ultrasonic reflected signal from each of the sampling points on the observed section are obtained. Hereinbelow this set of data is called a phase signal. MTI filters 83 and 93 provided with delaying elements giving a delay equal to the transmission repetition period t for a sampling point, respectively, calculate differences between the data of last time and the newest data. In this way $Q_i$ and $R_i$, which are outputs of the MTI filters 83 and 93, are phase signals, from which phase signals having a phase shift almost zero in a time interval t are removed. A main velocity calculator 100 calculates a phase shift in the time interval t by auto-correlation for the phase signals from each of the sampling points obtained from the MTI filters 83 and 93 and converts it into a velocity. However, usually transmission is repeated a plurality of times for a sampling point and phase shifts thus obtained are averaged to obtain an average velocity $V_i$ in this period of time. The velocity $V_i$ obtained by the main velocity calculator 100 is converted into a color tone signal consisting of 3 components of R, G and B in an indication controller. In the conventional color flow mapping apparatus this is written in the digital scan converter 50. Usually color tones, which are distinguished, depending on the sign of the velocity $V_i$, positive or negative, i.e. whether it is a flow approaching the ultrasonic probe or a flow away therefrom, are selected. The data of the B-mode image (gray scale data) indicated previously and the color data indicating this flow velocity are read-out from the digital scan converter 50 and given to a color monitor 70 through a color converter 55 effecting correction of a color signal suitable for the color monitor and a D/A converter 60.

Further the color display of the flow velocity can be effected by varying the color tone or the brilliance depending on not only the velocity signal $V_i$ described above but also the turbulence $T_i$ of the phase shift or the power $P_i$ of the phase signals. Although practical examples thereof will be described later, here calculation of these $T_i$ and $P_i$ will be described. The phase signals $Q_i$ and $R_i$, which have passed through the MTI filters 83 and 93, are inputted in a main turbulence calculator 101 and the turbulence $T_i$ of the phase shift for every time of the measurement for each of the sampling points is calculated according to a following formula:

$$T_i = \frac{1}{n} \sum_{j=1}^{n} (\theta_j - \theta)^2 \qquad (1)$$
$$= \frac{1}{n} \sum_{j=1}^{n} \theta_j^2 - \theta^2$$

where n: number of used data sets
$\theta_j$: phase shift obtained for every time of measurement
and $\theta$: average of phase shift That is, in the present embodiment, the variance $\sigma^2$ of the phase shift is calculated as turbulence of the phase shift.

Further a main power calculator 102 calculates the power $P_i$ from the two components $Q_{ij}$, $R_{ij}$ (j=1, 2, ..., n) of the phase signal for every time of the measurement for each of the sampling points, using a following formula:

$$P_i = \sum_{j=1}^{n} (Q_{ij}^2 + R_{ij}^2) \qquad (2)$$

The phase signals $A_i$ and $B_i$ are used before they are subjected to filtering by the MTI filters that the output of the main velocity calculator 100 is influenced by reflected waves from the body organs and that the apparatus is provided further with artifact detector 105 prohibiting the display of the flow velocity. That is, the phase signals $A_i$ and $B_i$ are coupled to a sub-velocity calculator 110 which effects calculations of the velocity similar to the main velocity calculator 100. That is, it calculates the phase shift in a time interval t by a self-correlation operation of the phase signals $A_i$ and $B_i$ and further averages phase shifts for every n repetitions of transmission for a same sampling point to obtain a second average velocity $V'_i$. A signal power $P_i'$ indicating the intensity of reflected waves for each of the sampling points is calculated by a sub-power calculator 111. The signal power $P_i'$ is obtained by using the phase signals $A_{ij}$ and $B_{ij}$ (j=1, 2, ..., n) for every time by a following formula:

$$P'_i = \sum_{j=1}^{n} (A_{ij}^2 + B_{ij}^2) \qquad (3)$$

The second velocity $V'_i$ obtained by the sub-velocity calculator 110 represents mainly the velocity of movements of the body organs. The flow velocity $V_i$ obtained by the main velocity calculator is the velocity calculated from the phase signals, which have passed through the MTI filters and it is influenced strongly by the movements of the body organs, when the absolute value of $V'_i$ is great. Therefore, in the present embodiment, the absolute value of the output $V'_i$ of the sub-velocity calculator 110 is compared with a predetermined velocity threshold $V'_{th}$. When the absolute value of $V'_i$ exceeds $V'_{th}$, a prohibition signal INH is issued, which prohibits the flow velocity $V_i$ at that sampling point from being displayed on a screen. Although if the output of the comparator 120 is used as an inhibition signal as it is, the same effect can be obtained, too, in the present embodiment, the output $P'_i$ of the sub-power calculator 111 is taken into account together for the inhibition signal. That is, the output $P_i'$ of the sub-power calculator 111 is compared with a power threshold value $P'_{th}$ by a comparator 121. When $P'_i$ is smaller than $P'_{th}$, the inhibition output INH is canceled by an inhibit gate 125, because in the case where the intensity of the reflected waves is low, the reflected waves from the blood flow is predominant rather than the reflected waves from the body organs and it is possible to judge that the artifact due to movement of the body organs is not mixed in the output $V_i$ of the main velocity calculator, even if $V_i'$ is great. When the prohibition signal INH is outputted, the indication controller 130 puts the value of the color signal at zero. In this way color data of the sampling point, to which the digital scan converter corresponds, are made zero and the artifact due to movement of the body organs is removed from the image of the flow velocity distribution displayed by color tones.

Figure 2:
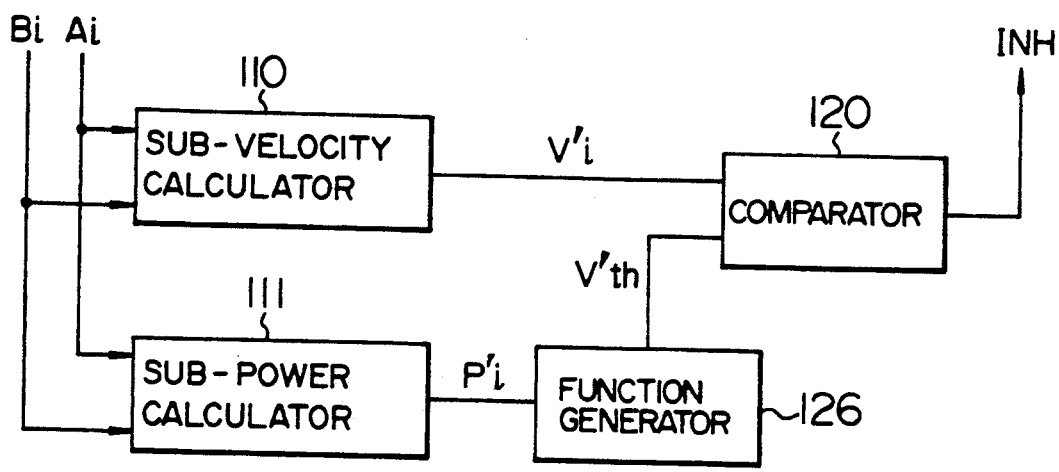
FIG. 2 is a block diagram indicating a principal part of another embodiment.
Figure 3:
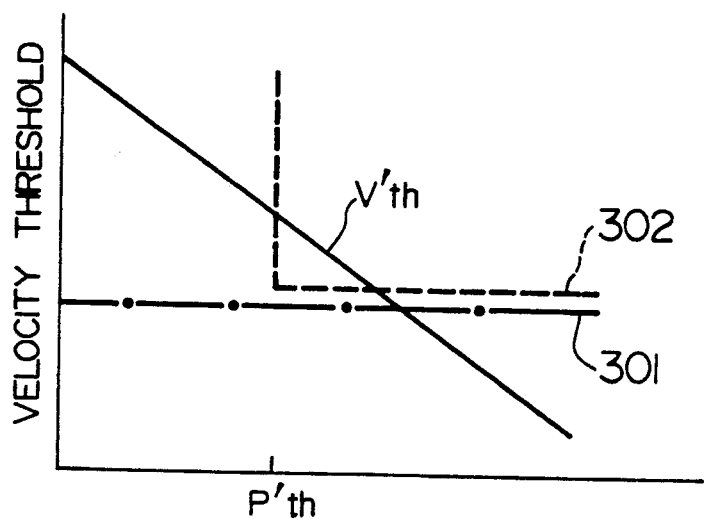
FIG. 3 shows a characteristic curve indicating velocity thresholds used in these embodiments.

FIG. 2 indicates another embodiment of the artifact detecting means 105. In the present embodiment, the velocity threshold $V'_{th}$ for generating the prohibition signal used for the comparator 120 is not constant, but given as a function of $P_i'$. That is, the output $P_i'$ of the sub-power calculator 111 is given to a function generator 126 and a velocity threshold $V'_{th}$ depending on $P_i'$ generated by the function generator 126 is outputted. When the absolute value of $V_i'$ is greater than this $V'_{th}$, the prohibition signal INH is outputted from the comparator 120 to the indication controller 130. The relation between the input $P_i'$ and the output $V'_{th}$ of the function generator 126 is indicated by a full line in FIG. 3 and $V'_{th}$ decreases with increasing $P_i$. Further, a chain dotted line 301 in FIG. 3 indicates characteristics of the substantial threshold $V'_{th}$, in the case where the output of the comparator 120 in the embodiment indicated in FIG. 1 is used directly for the inhibition signal INH, while a broken line 302 indicates characteristics of $V'_{th}$, when the output of the inhibit gate 125 in the embodiment indicated in FIG. 1 is used as the inhibition signal INH. The region on the upper side of all the lines represents the region, where the color display of the flow speed $V_i$ is inhibited. If the velocity threshold depending on the value of $P_i'$ is adopted as in the embodiment indicated in FIG. 2, it is possible to judge still more precisely presence or absence of the mixing of the artifact than in the embodiment indicated in FIG. 1.

Figure 4:
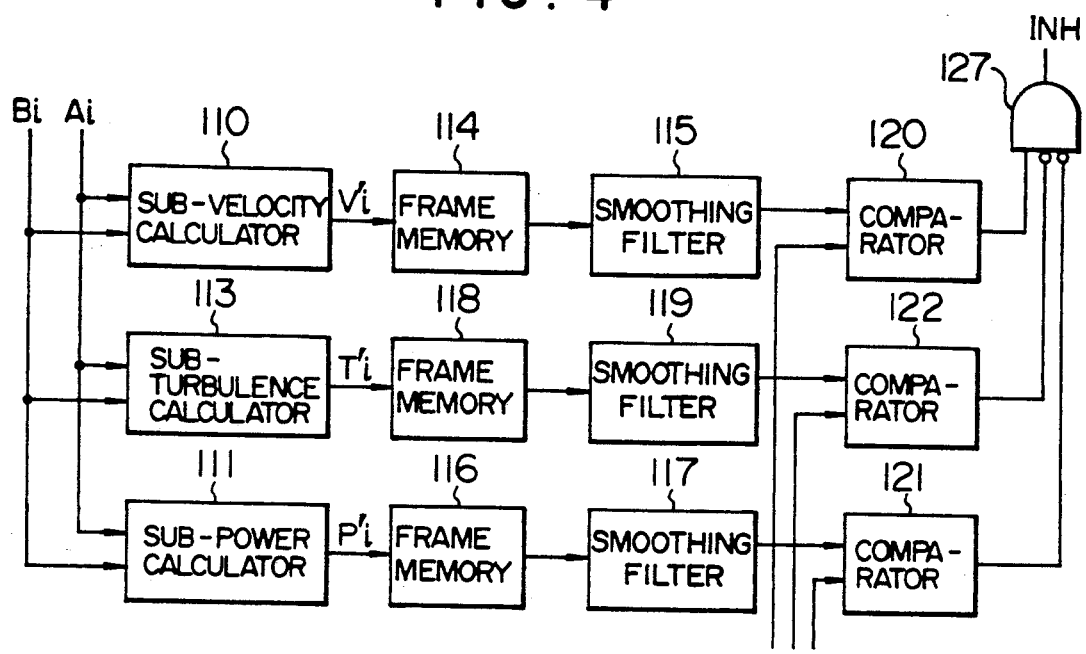
FIG. 4 is a block diagram indicating a principal part of still another embodiment.

FIG. 4 shows still another embodiment of the artifact detector. In the present embodiment, in addition to the sub-velocity calculator 110 and the sub-power calculator 111 there is disposed further a sub-turbulence calculator 113. The sub-turbulence calculator 113 calculates turbulence $T'_i$ of values produced in measurements repeated a plurality of times for the phase shifts indicated by the phase signals $A_i$ and $B_i$ for each of the sampling points. The method for calculating the turbulence $T_i'$ in the sub-turbulence calculator 113 is similar to that used in the main turbulence calculator and it is given by a following formula;

$$T'_i = \frac{1}{n} \sum_{j=1}^{n} (\theta'_j - \theta')^2 \qquad (4)$$
$$= \frac{1}{n} \sum_{j=1}^{n} \theta'_j{}^2 - \theta'^2$$

where n: number of used data sets, $\theta_j'$: phase shift indicated by $A_j$, $B_j$ for every time of measurements, and $\theta'$: average of phase shift.

Further, in the embodiment indicated in FIG. 4, the outputs $V_i'$, $T_i'$ and $P_i'$ of the sub-velocity calculator 110, the sub-power calculator 111 and the sub-turbulence calculator 113 are stored in frame memories 114, 116 and 118, respectively, having memory areas corresponding to the whole B-mode section. When $V_i'$, $T_i'$ and $P_i'$ (i=1, 2, ..., N) for all the sampling points in the section are stored in the memories 114, 116 and 118, respectively, presence or absence of the artifact is judged for each of the sampling points by using data, which have passed through smoothing filters 115, 117 and 119. The smoothing filters 115, 117 and 119 form arithmetic averages of data of a relevant sampling point and data of points adjacent thereto to obtain a data value for the relevant sampling point. That is, peculiar values in the data distribution are corrected by forming moving average of the data. The velocity $V_i'$, which has passed through the smoothing filter 115 is compared with the velocity threshold $V_{th}'$ in the comparator 120 similarly to the embodiment indicated in FIG. 1. When $V_i'$ is greater than $V'_{th}$, the inhibition signal INH prohibiting to display the flow velocity $V_i$ at that sampling point is issued. However, when the value of the turbulence $T_i'$, which has passed through the smoothing filter 117, is greater than a turbulence threshold $T'_{th}$ or when the value of the power $P_i'$, which has passed through the smoothing filter, is smaller than a power threshold $P'_{th}$, it is prevented by the inhibit gate 127 to output the inhibition signal INH. In these cases, regardless of the magnitude of the velocity $V_i'$, the velocity $V_i$ obtained by the main velocity calculator 100 is displayed in the color tone. In the present embodiment, since data indicating turbulence of the phase shift indicated by the phase signals, which have not passed through the MTI filters, are taken into account in the judgement of the mixing of the artifact, the number of cases where, although the velocity $V_i'$ outputted by the main velocity calculator represents correctly the velocity of the blood flow, the display thereof is inhibited, is further reduced. Further, since judgment of the mixing of the artifact is effected, after data on the velocity $V_i'$, the turbulence $T_i'$ and the power $P_i'$ have been subjected to spatial smoothing processing, erroneous judgment due to incorrect data existing locally can be prevented.

Figure 5:
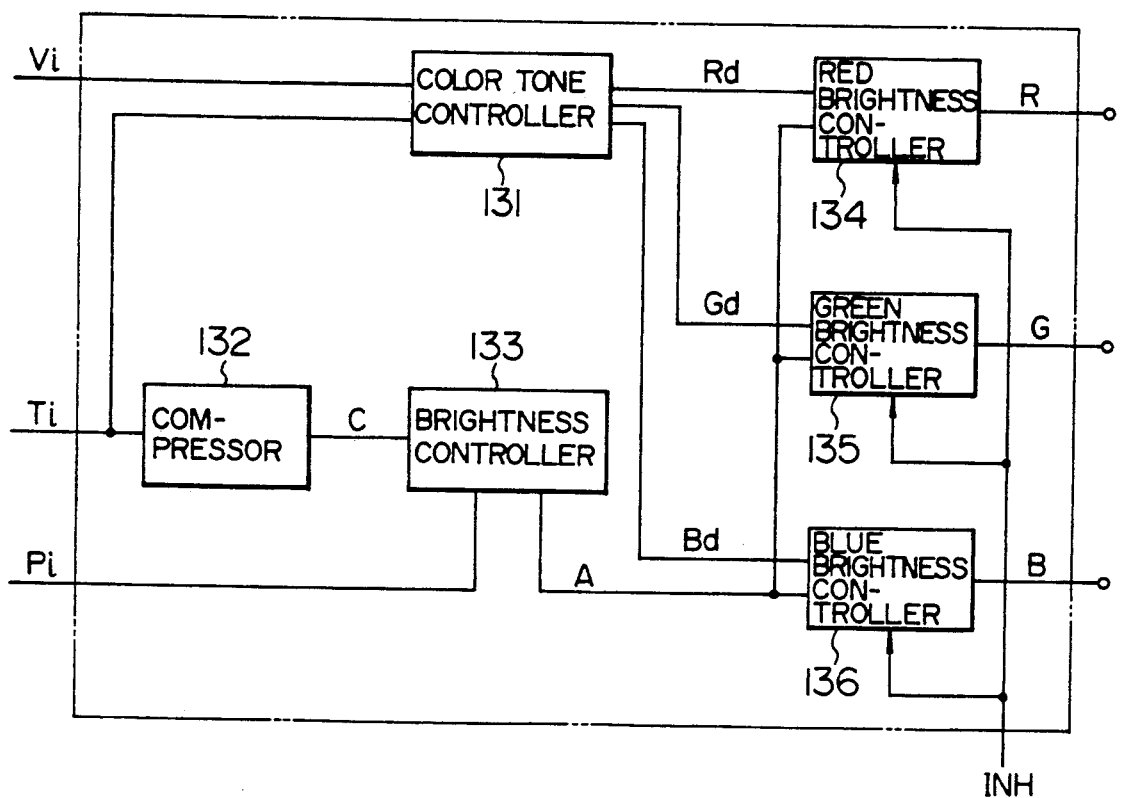
FIG. 5 is a block diagram indicating a principal part of still another embodiment.
Figure 6:
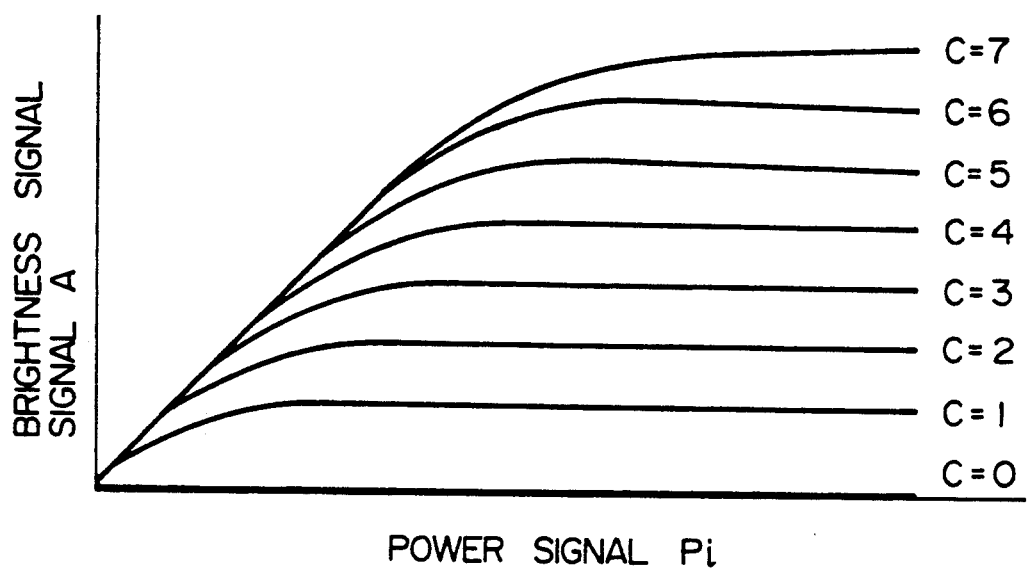
FIG. 6 shows characteristic curves for the brilliance control used in the embodiment indicated in FIG. 5.

FIG. 5 indicates the circuit construction of the principal part of the indication controller 130 used in the different embodiments described above. Data on the velocity $V_i$ obtained by the main velocity calculator (100 in FIG. 1) are inputted in a color tone controller 131. In order to choose a color corresponding to the value of the velocity, the color tone controller generates signals Rd, Gd and Bd indicating brightness distribution of different colors of red, green and blue. A final red signal R is calculated by a red brightness controller 134 from a product of the red signal Rd by a brightness control signal A indicating a total display brightness. Similarly a green brightness controller 135 outputs a product of Gd by A as a green signal G and a blue brightness controller 136 outputs a product of Bd by A as a blue signal B. However, when the inhibition signal INH described above is issued, all the signals R, G and B are cleared to be zero. The value of the brightness control signal A is determined on the basis of the values of the power $P_i$ from the main power calculator 102 and the turbulence $T_i$ from the main turbulence calculator 101 as indicated below. At first, the turbulence $T_i$ is led to a compressor 132 and converted into a signal C, in which the region, where the degree of the mixing of the artifact due to movement of the body organs in the flow speed, is left and the other region is compressed. The signal C has 8-step level from C=0 to C=7. This signal C and the power $P_i$ are led to a brightness controller 132. The brightness controller issues the brightness control signal A having an intensity varying according to characteristics indicated in FIG. 6, responding to the values of the signal C and the power $P_i$. That is, the intensity of the signal A increases with the increasing value of the power $P_i$ and it is saturated in a region, where the power $P_i$ is great. Further the upper limit of the signal A is smaller with the decreasing value of the signal C. When such a brightness control signal A is adopted following two effects can be obtained.

(1) Since the display brightness of the flow velocity for each of the sampling points depends on the intensity of the reflected waves from the blood flow at that point, a display reflecting the distribution of the flow is obtained.

(2) The signal from a sampling point, for which the turbulence in the phase shift is small, is very probably subjected to influences of reflected waves from the body organ. Since a display brightness of many steps responding to the value of this turbulence is used, the artifact due to movement of the body organs as a whole is reduced and it is possible to obtain a display of the flow distribution, in which necessary information is not removed.

As described above, it is possible to display the most appropriate blood flow distribution, from which the artifact is removed, by applying two measures to a color mapping apparatus, which measures are prohibition of the velocity display by detecting the mixing of the artifact, using a phase signal, which has not passed through any MTI filter, and multi-step control of the display brightness, depending on the degree of the turbulence in a phase signal, which has passed through an MTI filter. However, even by using only either one of the measures, considerable effect can be obtained for removing the artifact. Further, apart from realizations indicated in the embodiments described above, various modifications thereof are possible. For example, all of the data $V'_i$, $T'_i$ and $P'_i$ in FIG. 4 and the data $T_i$ and $P_i$ in FIG. 1 can be used as variables or parameters for determining the value of brightness control signal A. In such a modifications, a ROM storing a multi-variable analysis function, is provided instead of comparators 120, 121 and 122 and of inhibit gate 127 shown in FIG. 4. A value of brightness control signal A is read out from the ROM by addressing the variables $V'_i$, $T'_i$, $P'_i$, $T_i$ and $P_i$.

We claim:

1. An ultrasonic flow mapping apparatus comprising:

ultrasonic transmitting/receiving means for transmitting repeatedly a pulsed ultrasonic beam scanning successively a predetermined cross-section of an object to be examined and detecting reflected waves from a plurality of positions on said cross-section;

phase detecting means for forming ultrasonic phase signals indicating amplitudes and phases from detection signals of said reflected waves for each of said plurality of positions;

filter means for removing signal components near a position, where a phase shift is zero, from each of said ultrasonic phase signals;

first velocity calculating means for calculating phase shifts corresponding to a transmission interval at corresponding positions from the ultrasonic phase signals, which have passed through said filter means, respectively, to derive first velocity signals;

artifact detecting means including second velocity calculating means for calculating phase shifts corresponding to said transmission interval from the ultrasonic phase signals formed by said phase detecting means, respectively, to derive second velocity signals therefrom, and detecting by using values of said second velocity signals whether artifact is mixed in each of said first velocity signals;

indication control means for forming display signals from said first velocity signals and controlling the display signals for a corresponding position by using a detection output of said artifact detecting means; and a display device for displaying said display signal formed and controlled by said indication control means.

2. An ultrasonic flow mapping apparatus according to claim 1, wherein said artifact detecting means issues a prohibition signal, which prohibits to display a velocity at that position, when said second velocity signals exceed a first threshold.

3. An ultrasonic flow mapping apparatus according to claim 2, wherein said artifact detecting means includes further a power detector for detecting power of said ultrasonic phase signals formed by said phase detecting means and logic means for canceling said prohibition signal, when said power is lower than a second threshold.

4. An ultrasonic flow mapping apparatus according to claim 2, wherein said artifact detecting means includes further a turbulence detector for detecting turbulence in the phase shift of said ultrasonic phase signals formed by said phase detecting means and logic means for canceling said prohibition signal, when said turbulence is higher than a third threshold.

5. An ultrasonic flow mapping apparatus according to claim 1, wherein said artifact detecting means compares each of said second velocity signals with said first threshold, which is function of the power of said ultrasonic phase signals obtained by said phase detector, and issues a prohibition signal, which prohibits to display the velocity at the corresponding position, when said second velocity signals are higher than a first threshold.

6. An ultrasonic flow mapping apparatus according to claim 5, wherein said first threshold is issued according to a function decreasing with the increasing power of said ultrasonic phase signals.

7. An ultrasonic flow mapping apparatus comprising:
ultrasonic transmitting/receiving means for transmitting repeatedly a pulsed ultrasonic beam scanning successively a predetermined cross-section of an object to be examined and detecting reflected waves from a plurality of positions on said cross-section;

phase detecting means for forming ultrasonic phase signals indicating amplitudes and phases from detection signals of said reflected waves for each of said plurality of positions;

filter means for removing signal components near a position, where a phase shift is zero, from each of said ultrasonic phase signals;

first velocity calculating means for calculating phase shifts corresponding to a transmission interval at corresponding positions from the ultrasonic phase signals, which have passed through said filter means, respectively, to derive first velocity signals;

artifact detecting means including second velocity calculating means for calculating phase shifts corresponding to said transmission interval from the ultrasonic phase signals formed by said phase detecting means, respectively, to derive second velocity signals therefrom, and detecting by using values of said second velocity signals whether artifact is mixed in each of said first velocity signals or not;

indication control means generating a color brightness control signal, which specifies a color tone corresponding to values of said first velocity signals and a brightness corresponding to detection signals of said artifact detecting means; and a color display device for displaying flow velocity for each of a plurality of positions, responding to said color brightness control signal given by said indication control means.

8. An ultrasonic flow mapping apparatus comprising:
ultrasonic transmitting/receiving means for transmitting repeatedly a pulsed ultrasonic beam scanning successively a predetermined cross-section of an object to be examined and detecting reflected waves from a plurality of positions on said cross-section;

phase detecting means for forming ultrasonic phase signals indicating amplitudes and phases from detection signals of said reflected waves for each of said plurality of positions;

filter means for removing signal components near a position, where a phase shift is zero, from each of said ultrasonic phase signals;

first velocity calculating means for calculating a plurality of times phase shifts corresponding to a transmission interval at corresponding positions from the ultrasonic phase signals, which have passed through said filter means, respectively, to derivate an average of phase shifts measured a plurality of times as a velocity;

turbulence calculating means for calculating turbulence in values of said phase shifts measured a plurality of times;

power calculating means for calculating a sum of powers of phase signals giving said phase shifts measured a plurality of times;

indication control means generating a color brightness control signal, which specifies a color tone corresponding to outputs of said first velocity calculating means and a brightness corresponding to values of said turbulence and power; and a color display device for displaying flow velocity for each of a plurality of positions, responding to said color brightness control signal given by said indication control means.

9. An ultrasonic flow mapping apparatus according to claim 8, wherein said color brightness control signal specifies a lower brightness for decreasing value of said turbulence.

10. An ultrasonic flow mapping apparatus according to claim 8, wherein said color brightness control signal specifies a lower brightness for decreasing value of said power.

11. An ultrasonic flow mapping apparatus according to claim 8, further comprising:

artifact detecting means including second velocity calculating means for calculating phase shifts corresponding to said transmission interval from the ultrasonic phase signals formed by said phase detecting means, respectively, to derivate second velocity signals therefrom, and detecting by using values of said second velocity signals whether artifact is mixed in each of said first velocity signals or not, wherein the brightness of said indication control means corresponds to detection signals of said artifact detecting means.

* * * * *